(12) United States Patent
Ford et al.

(10) Patent No.: US 9,249,155 B2
(45) Date of Patent: Feb. 2, 2016

(54) THIENO [2, 3-D] PYRIMIDINE DERIVATIVES AND THEIR USE TO TREAT ARRHYTHMIA

(75) Inventors: John Ford, Hemingford Grey (GB); Derek Edward John, Sawston (GB)

(73) Assignee: XENTION LIMITED, Cambridge (GB)

( * ) Notice: Subject to any disclaimer, the term of this patent is extended or adjusted under 35 U.S.C. 154(b) by 124 days.

(21) Appl. No.: 14/008,776

(22) PCT Filed: Mar. 29, 2012

(86) PCT No.: PCT/GB2012/050710
§ 371 (c)(1),
(2), (4) Date: Apr. 4, 2014

(87) PCT Pub. No.: WO2012/131379
PCT Pub. Date: Oct. 4, 2012

(65) Prior Publication Data
US 2014/0206703 A1    Jul. 24, 2014

(30) Foreign Application Priority Data
Apr. 1, 2011 (GB) .................................. 1105659.5

(51) Int. Cl.
*C07D 495/04* (2006.01)
(52) U.S. Cl.
CPC .................................... *C07D 495/04* (2013.01)
(58) Field of Classification Search
CPC ..................................................... C07D 495/04
See application file for complete search history.

(56) References Cited

U.S. PATENT DOCUMENTS

| | | | |
|---|---|---|---|
| 2,839,540 A | 6/1958 | Peter |
| 4,196,207 A | 4/1980 | Webber |
| 5,681,839 A | 10/1997 | Crossley |
| 5,753,676 A | 5/1998 | Crossley |
| 5,821,251 A | 10/1998 | Crossley |
| 5,935,945 A | 8/1999 | Lynch |
| 5,969,017 A | 10/1999 | Lynch |
| 6,066,631 A | 5/2000 | Tanikawa |
| 6,083,986 A | 7/2000 | Castle |
| 6,194,458 B1 | 2/2001 | Baker |
| 6,221,866 B1 | 4/2001 | Brendel |
| 6,333,337 B1 | 12/2001 | Gross |
| 6,395,730 B1 | 5/2002 | Gross |
| 6,531,495 B1 | 3/2003 | Brendel |
| 6,555,574 B1 | 4/2003 | Tanikawa |
| 6,589,983 B1 | 7/2003 | Tanikawa |
| 6,677,371 B1 | 1/2004 | Tanikawa |
| 6,887,870 B1 | 5/2005 | Ahmad |
| 6,982,279 B2 | 1/2006 | Peukert |
| 2002/0006929 A1 | 1/2002 | Gross |
| 2002/0123494 A1 | 9/2002 | Heltsch |
| 2002/0193422 A1 | 12/2002 | Brendel |
| 2003/0013719 A1 | 1/2003 | Peukert |
| 2003/0022890 A1 | 1/2003 | Atwal |
| 2003/0060470 A1 | 3/2003 | Peukert |
| 2003/0114499 A1 | 6/2003 | Brendel |
| 2003/0187033 A1 | 10/2003 | Brendel |
| 2004/0044030 A1 | 3/2004 | Claremon |
| 2004/0063731 A1 | 4/2004 | Eggenweiler |
| 2004/0068002 A1 | 4/2004 | Ohara |
| 2004/0068120 A1 | 4/2004 | Peukert |
| 2004/0072880 A1 | 4/2004 | Lloyd |
| 2004/0152763 A1 | 8/2004 | Ohara |
| 2005/0026935 A1 | 2/2005 | Ford |
| 2006/0040961 A1 | 2/2006 | Buchanan |
| 2007/0287717 A1 | 12/2007 | Fanning et al. |
| 2010/0041695 A1 | 2/2010 | Ford et al. |

FOREIGN PATENT DOCUMENTS

| | | |
|---|---|---|
| DE | DD226893 | 9/1985 |
| RU | 2116309 | 7/1998 |
| WO | WO 97/07119 | 2/1997 |
| WO | WO0012492 | 3/2000 |
| WO | WO 01/46155 | 6/2001 |
| WO | WO 2004/111057 | 12/2004 |
| WO | WO 2005/066182 | 7/2005 |
| WO | WO 2006/061642 | 6/2006 |
| WO | WO 2007/084815 | 7/2007 |
| WO | 2011026741 | 3/2011 |

OTHER PUBLICATIONS

Amos, Gregory, J., et al., Differences between outward currents of human atrial and subepicardial ventricular myocytes, Journal of Physiology, 1996, 491.1, 31-50.
Armstrong, Clay, M., et al., Voltage-gated ion channels and electrical excitability, Neuron, Mar. 1998, vol. 20, 371-380.
Bachmann, Alexander, et al., Characterization of a novel Kv1.5 channel blocker in Xenopus oocytes, CHO cells, human and rat cardiomyocytes, Naunyn-Schmiedeberg's Arch Pharmacol, 2001, 364, 472-478.
Brendel, Joachim, et al., Blockers of the Kv1.5 channel for the treatment of atrial arrhythmias, Expert Opin. Ther. Patents, 2002, 12(11), 1589-1598.
Colatsky, Thomas, J., PhD., et al., Channel specificity in antiarrhythmic drug action, Circulation, vol. 82, No. 6, Dec. 1990, 2235-2242.
Courtemanche, M., et al., Ionic targets for drug therapy and atrial vibrillation-induced electrical remodeling; insights from a mathematical model, Cardiovascular Research, 1999, 42, 477-489.
Dobrev, D., Md, et al., The G protein-gated potassium current IK,ACh is constitutively active in patients with chronic atrial fibrillation, Circulation, Dec. 13, 2005, 3697-3706.
English abstract for DD226893, 1985.
English Abstract Abstract for RU2116309, 1998.

(Continued)

*Primary Examiner* — James D Anderson
(74) *Attorney, Agent, or Firm* — Baker Botts L.L.P.

(57) ABSTRACT

The present invention relates to thienopyrimidine compounds which are potassium channel inhibitors. Pharmaceutical compositions comprising the compounds and their use in the treatment of arrhythmia are also described.

10 Claims, No Drawings

(56) References Cited

OTHER PUBLICATIONS

Fedida, D., et al., Identity of a novel delayed rectifier current from human heart with a cloned K+ channel current, Circulation Research, vol. 73, No. 1, Jul. 1993, 210-216.
Feng, Jianlin, et al., Antisense oligodeoxynucleotides directed against Kv1.5 mRNA specifically inhibit ultrarapid delayed rectifier K+ current in cultured adult human atrial myocytes, Circulation Research, vol. 80, No. 4, Apr. 1997, 572-579.
Feng, Jianlin, et al., Effects of class III antiarrhythmic drugs on transient outward and ultra-rapid delayed rectifier currents in human atrial myocytes, The Journal of Pharmacology and Experimental Therapeutics, vol. 281, No. 1, 1997, 384-391.
Ford, John, W., et al., Potassium channels: Gene family, therapeutic relevance, high-throughput screening technologies and drug discovery, Progress on Drug Research, vol. 58, 2002, 133-168.
Godreau, David, et al., Mechanisms of action of antiarrhythmic agent bertosamil on hKv1.5 channels and outward potassium current in human atrial myocytes, JPET, vol. 300, No. 2, 2002, 612-620.
Gutman, George, A., International union of pharmacology. XLI. Compendium of voltage-gated ion channels: Potassium channels, Pharmacological Reviews, vol. 55, No. 4, 2003, 583-586.
Hebert, Steven, C., MD, General principles of the structure of ion channels, The American Journal of Medicine, vol. 104, Jan. 1998, 87-98.
Hosni, Hanaa, M., et al., Thienopyrimidines II: Synthesis of newer thieno[2,3-d]-pyrimidines and their quaternized derivatives with molluscicidal activity, Acta Poloniai Pharmaceutica—Drug Research, vol. 56, No. 1, 1999, 49-56.
Hozien, Z.A., et al., Synthesis and application of some new thienopyrimidine derivatives as antimicrobial agents, Synthetic Communications, 26(20), 1996, 3733-3755.
Ismail, Khadiga, A., et al., Synthesis and antimicrobial activity of some tetramethylenethieno[2,3-d]pyrimidine derivatives, IL FARMACO, 50(9), 1995, 611-616.
Jordis, Ulrich, et al., 7,9-dideaza-9-thiaadenines, Vestn. Slov. Kem. Drus., 33/3/1986, 217-238.
Katada, Jun, et al., Cytotoxic effects of NSL-1406, a new thienopyrimidine derivative, on leukocytes and osteoclasts, Bioorganic & Medicinal Chemistry Letters, 9, 1999, 797-802.
Knobloch, Karsten, et al., Electrophysiological and antiarrhythmic effects of the novel /Kur channel blockers, S9947 and S20951, on left vs. right pig atrium in vivo in comparison with the /Kr blockers dofetilide, azimilide, d,l-sotalol and ibutilide, Naunyn-Schmiedeberg's Arch Pharmacol, 366, 2002, 482-487.
Konno, Shoetsu, et al., Synthesis of thieno[2,3-d]pyrimidine derivatives and their antifungal activities, Yakugaku Zasshi, vol. 109(7), 1989, 464-473.
Li, Gui-Rong, et al., Evidence for two components of delayed rectifier K+ current in human ventricular myocytes, Circulation Research, vol. 78, No. 4, Apr. 1996, 689-696.

Malayev, A.A., et al., Mechanism of clofilium block of the human Kv1.5 delayed rectifier potassium channel, Molecular Pharmacology, 47, 1995, 198-205.
Marban, Eduardo, Cardiac channelopathies, Nature, vol. 415, Jan. 10, 2002, 213-218.
Matsuda, Tomoyuki, et al., Inhibition by a novel anti-arrhythmic agent, NIP-142, of cloned human cardiac K+ channel Kv1.5 current, Life Sciences 68, 2000, 2017-2024.
Moneer, A. A., et al., Reaction of 3-amino and 4-hydrazino-5,6-tetramthylenethieno [2,3-d] pyrimidine derivatives with azlactones, Egypt. J. Pharm. Sci., 34, No. 4-6, 1993, 599-609.
Munchhof, Michael, J., Design and SAR of thienopyrimidine and thienopyridine inhibitors of VEGFR-2 kinase activity, Bioorganic & Medicinal Chemistry Letters, 14, 2004, 21-24.
Nattel, Stanley, et al., Cardiac ultrarapid delayed rectifiers: A novel potassium current family of functional similarity and molecular diversity, Cell Physiol Biochem, 9, 1999, 217-226.
Nattel, Stanley, Therapeutic implications of atrial fibrillation mechanisms: can mechanistic insights be used to improve AF management?, Cardiovascular Research, 54, 2002, 347-360.
Noravyan, A.S., et al., Synthesis and antispasmodic activity of 4-alkyl(aryl)amino-6,6-dimethyl-5,6-dihydro-8h-pyrano(thiopyrano) [3,4-b]thieno[5,4-d]pyrimidines, Khimiko-Farmatsevticheskii Zhurnal, No. 9, Sep. 1977, 38-43.
Peukert, Stefan, et al., Identification, synthesis and activity of novel blockers of the voltage-gated potassium channel Kv1.5, J. Med. Chem., 46, 2003, 486-498.
Ram, Vishnu, J., Thieno[2,3-d]pyrimidines as potential chemotherapeutic agents, J. Heterocyclic Chem., 18, 1981, 1277-1280.
Ram, Vishnu, Ji, Thieno[2,3-d]pyrimidines as potential chemotherapeutic agents, Arch Pharm. (Weinheim) 312, 1979, 19-25.
Search Report for GB1105659.5 dated Jun. 27, 2011.
Shehata, I.A., Synthesis, antitumor and anti-HIV-1 testing of certain theino[2,3-d]pyrimidine, thieno[2,3-d]imidazo[1,2-c] pyrimidine and thieno[2,3-d]thiazine derivatives, Med Chem Res, 1996, 148-163.
Shieh, Char-Chang, et al., Potassium channels: molecular defects, diseases, and therapeutic opportunities, Pharmacological Reviews, vol. 52, No. 4, 2000, 557-593.
Stewart, Andrew, O., et al., Discovery of inhibitors of cell adhesion molecule expression in human endothelial cells. 1. Selective inhibition of ICAM-1 and E-selectin expression, J. Med. Chem., 44, 2001, 988-1002.
Wang, Zhiguo, et al., Effects of flecainide, quinidine, and 4-aminopyridine on transient outward and ultrarapid delayed rectifier currects in human atrial myocytes, The Journal of Pharmacology and Experimental Therapeutics, vol. 272, No. 1, 1995, 184-196.
Wang, Zhiguo, et al., Sustained depolarization-induced outward current in human atrial myocytes, Circulation Research, vol. 73, No. 6, Dec. 1993, 1061-1076.
Wirth, Klaus, J., Atrial effects of the novel K+-channel-blocker AVE0118 in anesthetized pigs, Cardiovascular Research, 60, 2003, 298-306.
Xu, Acta Genetica Sinica, 27 (3), 2000, 195-201.

THIENO [2, 3-D] PYRIMIDINE DERIVATIVES AND THEIR USE TO TREAT ARRHYTHMIA

TECHNICAL FIELD

The present invention relates to thienopyrimidine compounds which are potassium channel inhibitors. Pharmaceutical compositions comprising the compounds and their use in the treatment of arrhythmia are also provided.

BACKGROUND ART

Ion channels are proteins that span the lipid bilayer of the cell membrane and provide an aqueous pathway through which specific ions such as $Na^+$, $K^+$, $Ca^{2+}$ and $Cl^-$ can pass (Herbert, 1998). Potassium channels represent the largest and most diverse sub-group of ion channels and they play a central role in regulating the membrane potential and controlling cellular excitability (Armstrong & Hille, 1998). Potassium channels have been categorized into gene families based on their amino acid sequence and their biophysical properties (for nomenclature see Gutman et al., 2003).

Compounds which modulate potassium channels have multiple therapeutic applications in several disease areas including cardiovascular, neuronal, auditory, renal, metabolic and cell proliferation (Shieh et al., 2000; Ford et al., 2002). More specifically potassium channels such as Kv4.3, Kir2.1, hERG, KCNQ1/minK, and Kv1.5 are involved in the repolarisation phase of the action potential in cardiac myocytes. These potassium channels subtypes have been associated with cardiovascular diseases and disorders including long QT syndrome, hypertrophy, ventricular fibrillation, and atrial fibrillation, all of which can cause cardiac failure and fatality (Marban, 2002).

The human delayed rectifier voltage gated potassium channel subunit, Kv1.5, is exclusively expressed in atrial myocytes and is believed to offer therapeutic opportunities for the management of atrial fibrillation for several different reasons (see review of Brendel and Peukert, 2002): (i) There is evidence that Kv1.5 underlies the cardiac ultrarapid delayed rectifier ($Kv_{(ur)}$) physiological current in humans due to similar biophysical and pharmacological properties (Wang et al., 1993; and Fedida et al., 1993). This has been supported with antisense oligonucleotides to Kv1.5 which have been shown to reduce $Kv_{(ur)}$ amplitude in human atrial myocytes (Feng et al., 1997). (ii) electrophysiological recordings have demonstrated that $Kv_{(ur)}$ is selectively expressed in atrial myocytes, and therefore avoids inducing potentially fatal ventricular arrhythmia through interfering with ventricular repolarisation (Amos et al., 1996; Li et al., 1996; and Nattel, 2002). (iii) Inhibiting $Kv_{(ur)}$ in atrial fibrillation-type human atrial myocytes prolonged the action potential duration compared to normal healthy human atrial myocytes (Courtemanche et al., 1999). (iv) Prolonging the action potential duration by selectively inhibiting Kv1.5 could present safer pharmacological interventions for protecting against atrial re-entrant arrhythmias such as atrial fibrillation and atrial flutter compared to traditional class III antiarrythmics, by prolonging the atrial refractory period while leaving ventricular refractoriness unaltered (Nattel et al., 1999, Knobloch et al., 2002; and Wirth et al., 2003). Class III antiarrythmics have been widely reported as a preferred method for treating cardiac arrhythmias (Colatsky et al., 1990).

Traditional and novel class III antiarrythmic potassium channel blockers have been reported to have a mechanism of action by directly modulating Kv1.5 or $Kv_{(ur)}$. The known class III antiarrythmics ambasilide (Feng et al., 1997), quinidine (Wang et al., 1995), clofilium (Malayev et al., 1995) and bertosamil (Godreau et al., 2002) have all been reported as potassium channel blockers of $Kv_{(ur)}$ in human atrial myocytes. The novel benzopyran derivative, NIP-142, blocks Kv1.5 channels, prolongs the atrial refractory period and terminates atrial fibrillation and flutter in in vivo canine models (Matsuda et al., 2001), and 59947 inhibited Kv1.5 stably expressed in both Xenopus oocytes and Chinese hamster ovary (CHO) cells and $Kv_{(ur)}$ in native rat and human cardiac myocytes (Bachmann et al., 2001). Elsewhere, other novel potassium channel modulators which target Kv1.5 or $Kv_{(ur)}$ have been described for the treatment of cardiac arrhythmias, these include biphenyls (Peukert et al 2003), thiophene carboxylic acid amides (WO0248131), bisaryl derivatives (WO0244137, WO0246162), carbonamide derivatives (WO0100573, WO0125189) anthranillic acid amides (WO2002100825, WO02088073, WO02087568), dihydropyrimidines (WO0140231), cycloakyl derivatives (WO03063797), indane derivatives (WO0146155 WO9804521), tetralin benzocycloheptane derivatives (WO9937607), thiazolindone and metathiazanone derivatives (WO9962891), benzamide derivatives (WO0025774), isoquinoline derivatives (WO0224655), pyridazinones derivatives (WO9818475 WO9818476), chroman derivatives (WO9804542), benzopyran derivatives (WO0121610, WO03000675, WO0121609, WO0125224, WO02064581), benzoxazine derivatives (WO0012492), and the novel compound A1998 purified from Ocean material (Xu & Xu, 2000). General voltage gated potassium channel inhibitors have been reported which could also modulate Kv1.5 (U.S. Ser. No. 05/753,676, U.S. Ser. No. 05/821,251, EP0743936B).

Thienopyrimidines have been reported to be useful as anti-inflammatory, anti-fungal, anti-osteoporosis and anti-microbial agents, and as cardiovascular agents (acting through modulation of the phosphodiesterase group of enzymes or through modulation of the sodium/proton exchange system) amongst others.

Thieno[2,3-d]-pyrimidines substituted in the 4-position with an optionally substituted benzylamine or phenethylamine moiety and in the 5-position with a methyl group may serve as anti-inflammatory or anti-osteoporosis agents (Katada et al., 1999). Such compounds were shown to modulate the activity of several cell types including leukocytes, which originate from hematopoietic precursor cells in the bone marrow. Increased activity in leukocytes can lead to various inflammatory diseases; therefore compounds cytotoxic to leukocytes could function as anti-inflammatory drugs. Such compounds are thought to suppress cellular activity by binding to integrins on the surface of leukocytes and preventing downstream cellular signalling events. Thieno [2,3-d]pyrimidines substituted in the 4-position with heteroarylthiols, aryl thiols, arylmethyl thiols, heteroarylamines, benzylamine, hydroxyl and chloro groups may also be useful anti-inflammatory agents (Stewart et al., 2001). This series of compounds were shown to inhibit induced expression of cell adhesion molecules on the luminal surface of vascular endothelial thus preventing the adhesion of leukocytes at the site of inflammation.

Thieno[2,3-d]pyrimidines with a substituted hydrazine in the 4-position and a phenyl group in the 5 position (Hozien et al., 1996), tetrahydrobenzo[b]thieno[2,3-d]pyrimidines (Ismail et al., 1995), thieno[2,3-d]pyrimidines which have a hydrogen, chloro, hydrazine, heterocyclyl, amino, methyl, ethyl or phenyl group in the 2-position, an alkylamino, alkylarylamino, amino, dialkylamino or hydrazino substituent in the 4-position, a hydrogen or methyl group in the 5-position, a hydrogen, methyl acetamide or phenyl group in the 6-position or a tetramethylene in the 5,6-position (GB7549025), and the lead series of 5-phenyl- and 5,6-tetramethylenethieno [2,3-d]pyrimidines with methyl or phenyl in the 2-position and alkylamino or arylamino in the 4-position (Konno et al., 1989) have all been shown to have anti-microbial activity. Tetrahydrobenzothieno[2,3-d]pyrimidine with the 2-oxo-3-pyrrolidinylmethylene-hydrazino moiety in the 4-position showed some herbicidal activity against velvet leaf (Ram et al., 1981). It has also been reported that 4-chlorotetrahydrobenzothieno[2,3-d]pyrimidine is herbicidal, tetrahydrobenzothieno[2,3-d]pyrimidines with a thiol, hydrazine, 2-fluoroanilino, 3-fluoroanilino or 4-diethylanilino substituent in the 4-position are bactericidal against *Streptococcus fecales* and tetrahyrobenzothieno[2,3-d]pyrimidines with a 2,4-dichlorobenzylamino or 2-fluoroanilino substituent in the 4-position are fungicidal against *Pythium* (Ram, 1979). Thieno[2,3-d]pyrimidines with a hydrogen, hydroxyl, thiol, halogen or cyano group in the 2-position, alkylamino, arylalkylamino or hydroxyalkyl amino groups in the 4-position, a hydrogen, alkyl or halogen in the 5- and/or 6-position or alkylene in the 5,6-position have been reported as tick-control agents (AU 521790).

Elsewhere, tetrahydrobenzo[b]thieno[2,3-d]pyrimidines exhibited anti-tumour activity (Shehata et al., 1996) and analgesic activity half that of aspirin (Moneer et al., 1994), a series of thieno[2,3-d]pyrimidines with 4-alkylamino or arylamino, 5-H or 5-methyl, 6-methyl or 5,6-tetramethylene were shown to have potential as anticytokinins (Jordis et al., 1986), a series of 5,6-dimethyl-thieno[2,3-d]pyrimidines and 5,6-tetramethylenethieno[2,3-d]pyrimidines, both substituted in the 2-position with arylamines or heterocyclic amines and in the 4-position with arylamines displayed blood platelet aggregation inhibiting properties (DD 226893), pyrano- and thiopyrano[3,4-b]thieno[5,4-d]pyrimidines with the 4-position substituted with amino, butylamine, aniline, cyclohexylamine, benzylamine, phenethylamine and 2-hydroxyethylamine have been reported to exhibit anticonvulsive activity (Noravyan et al., 1977), and 4-[(Benzo-2,1,3-thiadiazolyl-4)amino]-5,6,7,8-tetrahydrobenzothieno-(2,3-d)-pyrimidine has been reported to possess anthelmintic activity in larval alveolar echinococcosis (RU 2116309).

Thieno[2,3-d]pyrimidines with a substituted amino group at the 4-position, hydrogen, alkyl or halo substitution at the 5 and 6-positions and an alkyl chain at the 2-position are claimed to be inhibitors of phosphodiesterase V and useful in the treatment of cardiovascular diseases and for disturbances in potency (DE10104802).

Elsewhere, 5-alkyl thieno[2,3-d]pyrimidines with a piperazinyl substituent at the 4-position were found to be inhibitors of the sodium/proton exchanger and useful in the treatment of various cardiovascular disorders, including angina pectoris and arrhythmia (WO 01/27107).

4-[(phenyl)amino]-thieno[2,3-d]pyrimidines bearing a 5-thiophenyl substituent and a 2-methyl substituent were found to have molluscicidal activity (Hosni et al, Acta Poloniae Pharmaceutica, 1999, 56(1), 49-56).

Recently thienopyrimidines have also been reported as potent VEGFR inhibitors (Munchhof, 2004).

Several publications disclose compounds which are indicated as acting on potassium channels. Thus, U.S. Pat. No. 6,531,495 discloses 2'-aminomethylbiphenyl-2-carboxamides, WO2002/100825 discloses anthranillic acid amides as antiarrhythmics and WO2002/036556 discloses acylaminoalkylbenzenesulfonamides as cardiovascular agents.

Thienopyrimidine compounds that are useful as potassium channel inhibitors, particularly for inhibiting potassium channels Kv1.5 or Kv$_{(ur)}$, are reported in WO 2004/111057.

DISCLOSURE OF THE INVENTION

A first aspect of the invention provides a compound of formula (Ia)

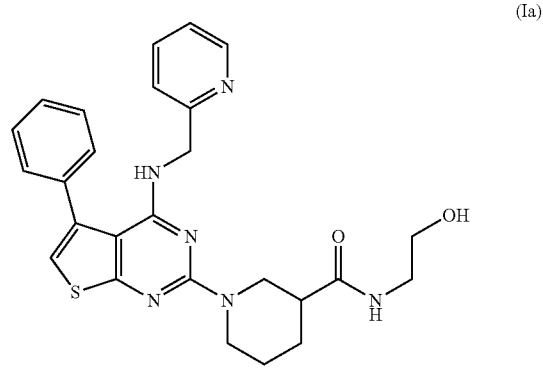 [SMILES: O=C(NCCO)C1CCCN(c2nc(NCc3ccccn3)c3c(-c4ccccc4)csc3n2)C1]

(Ia)

or a pharmaceutically acceptable ester or salt thereof.

In one embodiment, the compound is of formula (Ib)

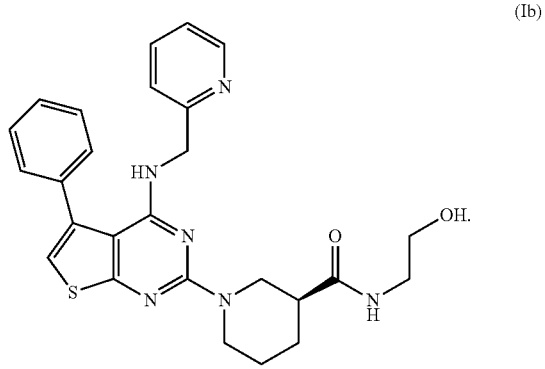 [SMILES: O=C(NCCO)[C@H]1CCCN(c2nc(NCc3ccccn3)c3c(-c4ccccc4)csc3n2)C1]

(Ib)

In another embodiment, the compound is of formula (Ic)

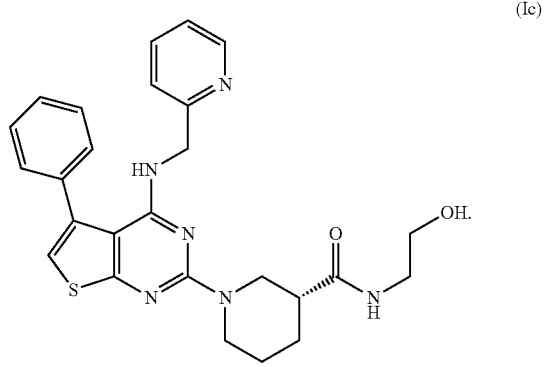 [SMILES: O=C(NCCO)[C@@H]1CCCN(c2nc(NCc3ccccn3)c3c(-c4ccccc4)csc3n2)C1]

(Ic)

In another embodiment, the compound of formula (Ia) comprises a mixture of the compounds of formulae (Ib) and (Ic). In a further embodiment, the compound of formula (Ia) comprises a racemic mixture of the compounds of formulae (Ib) and (Ic). In an alternative further embodiment, the compound of formula (Ia) comprises an enantiomeric excess of the compound of formula (Ib) or an enantiomeric excess of the compound of formula (Ic).

A second aspect of the invention provides a pharmaceutical composition comprising at least one of the above compounds and, optionally, one or more pharmaceutically acceptable excipients.

The compounds and compositions of the invention are potassium channel inhibitors that are particularly useful for inhibiting potassium channels Kv1.5 or $Kv_{(ur)}$ for the treatment of cardiac arrhythmia in the atria such as atrial fibrillation. This invention is not limited to treating cardiac arrhythmias, the compounds also being useful to treat diseases which require potassium channel inhibition (e.g. Shieh et al., 2000; Ford et al., 2002).

A third aspect of the invention therefore provides a method of potassium channel inhibition, comprising administering to a subject an effective amount of at least one compound or composition of the invention. This aspect of the invention further provides a compound or composition of the invention for use in potassium channel inhibition. In addition, this aspect of the invention further provides the use of a compound of the invention for the manufacture of a medicament for use in potassium channel inhibition. As used herein, a "method of potassium channel inhibition" and "use in potassium channel inhibition" include methods and uses for treating or preventing a disorder which responds to the inhibition of potassium channel function. The disorder may be arrhythmia.

The compounds of the invention have advantageous properties over those of the prior art, in particular in terms of potency and/or selectivity.

DETAILED DESCRIPTION OF THE INVENTION

Racemic Mixture

A "racemic mixture" contains approximately equal amounts of the compounds of formula (Ib) and formula (Ic). In other words, a compound or composition comprising a "racemic mixture" of the compounds of formula (Ib) and formula (Ic) contains an approximately 1:1, or 50:50, mixture of the compounds.

Enantiomeric Excess

A compound or composition comprising an "enantiomeric excess" of the compound of formula (Ib) or of the compound of formula (Ic) comprises more of that enantiomer than the other (also known as a scalemic mixture).

The enantiomeric excess is the excess of one compound over the other, expressed as a percentage of the whole. For instance, a 98:2 mixture of the compound of formula (Ib) to the compound of formula (Ic) has a 96% enantiomeric excess of the compound of formula (Ib). Thus, the compounds and compositions of the invention may comprise an enantiomeric excess of the compound of formula (Ib) of at least 5%, 10%, 15%, 20%, 25%, 30%, 35%, 40%, 45%, 50%, 55%, 60%, 65%, 70%, 75%, 80%, 85%, 90%, 95% or up to 100% (i.e. enantiomerically pure, up to the detection limit of purity). Alternatively, the compounds and compositions of the invention may comprise an enantiomeric excess of the compound of formula (Ic) of at least 5%, 10%, 15%, 20%, 25%, 30%, 35%, 40%, 45%, 50%, 55%, 60%, 65%, 70%, 75%, 80%, 85%, 90%, 95% or up to 100%.

R and S Nomenclature

As used herein, the term "R" or "S" isomer refers to the two possible enantiomers according to the Cahn-Ingold-Prelog system adopted by the International Union of Pure and Applied Chemistry (IUPAC). Thus, the compound of formula (Ib) is the "S-isomer" and the compound of formula (Ic) is the "R-isomer".

Pharmaceutically Acceptable Ester or Salt Thereof

The term "pharmaceutically acceptable ester" includes compounds of the invention in which the hydrogen atom of the alcohol group may be replaced to form an ester (e.g. the hydrogen atom may be replaced by —$C(O)C_{1-6}$alkyl).

The term "pharmaceutically acceptable salt" includes a salt prepared from pharmaceutically acceptable non-toxic acids or bases including inorganic or organic acids and bases.

Pharmaceutically acceptable acid addition salts of the compounds of the invention include, but are not limited to, those of inorganic acids such as hydrohalic acids (e.g. hydrochloric, hydrobromic and hydroiodic acid), sulfuric acid, nitric acid, and phosphoric acids. In addition, pharmaceutically acceptable acid addition salts of the compounds of the invention include, but are not limited to, those of organic acids such as aliphatic, aromatic, carboxylic and sulfonic classes of organic acids, examples of which include: aliphatic monocarboxylic acids such as formic acid, acetic acid, propionic acid or butyric acid; aliphatic hydroxy acids such as lactic acid, citric acid, tartaric acid or malic acid; dicarboxylic acids such as maleic acid or succinic acid; aromatic carboxylic acids such as benzoic acid, p-chlorobenzoic acid, phenylacetic acid, diphenylacetic acid or triphenylacetic acid; aromatic hydroxyl acids such as o-hydroxybenzoic acid, p-hydroxybenzoic acid, 1-hydroxynaphthalene-2-carboxylic acid or 3-hydroxynaphthalene-2-carboxylic acid; and sulfonic acids such as methanesulfonic acid, ethanesulfonic acid or benzenesulfonic acid. Other pharmaceutically acceptable acid addition salts of the compounds of the invention include, but are not limited to, those of glycolic acid, glucuronic acid, furoic acid, glutamic acid, anthranilic acid, salicylic acid, mandelic acid, embonic (pamoic) acid, pantothenic acid, stearic acid, sulfanilic acid, algenic acid, and galacturonic acid.

Pharmaceutically acceptable basic salts of the compounds of the invention include, but are not limited to, metal salts such as alkali metal or alkaline earth metal salts (e.g. sodium, potassium, magnesium or calcium salts) and zinc or aluminium salts. In addition, pharmaceutically acceptable basic salts of the compounds of the invention include, but are not limited to, salts formed with ammonia or pharmaceutically acceptable organic amines or heterocyclic bases such as ethanolamines (e.g. diethanolamine), benzylamines, N-methylglucamine, amino acids (e.g. lysine) or pyridine.

Synthesis

Compounds of formula (I) may be prepared as the racemate, as a scalemic mixture, or as a chirally pure enantiomer using routes described in the scheme 1 below:

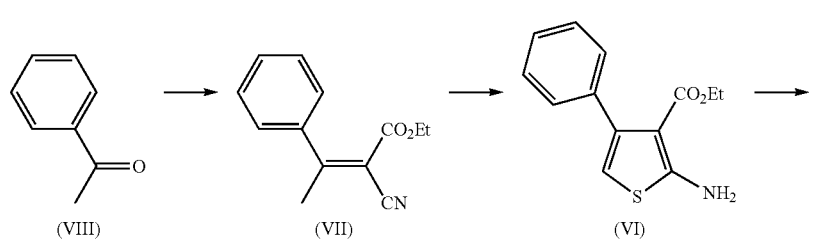

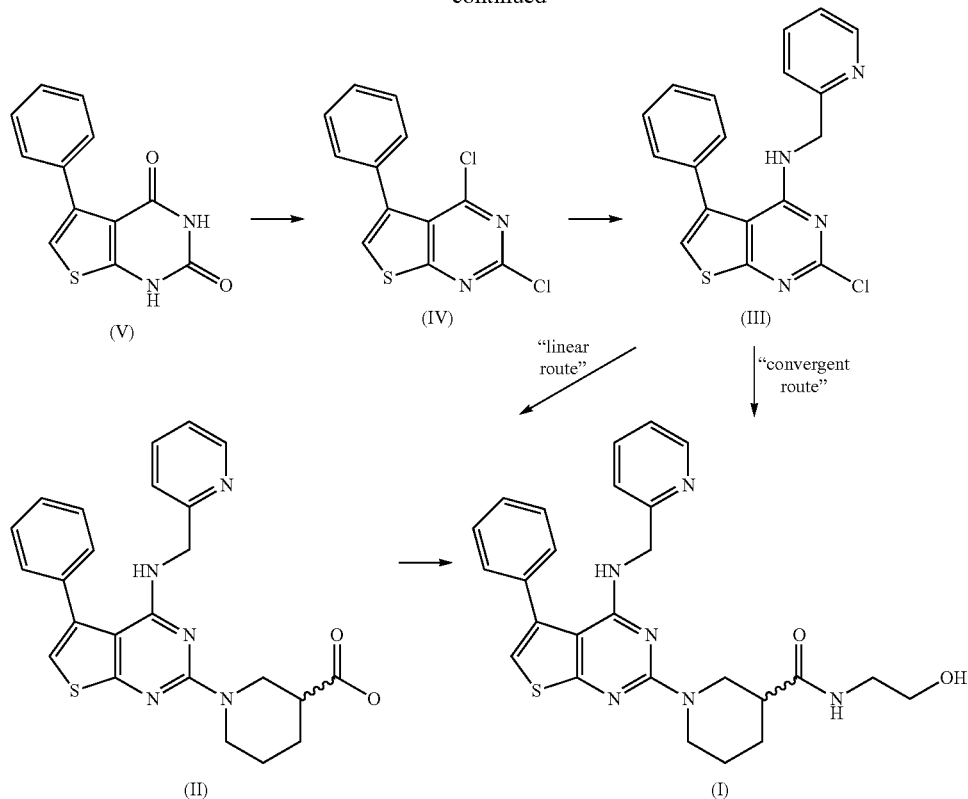

This includes the preparation of compounds of formula (I) using the "linear route" analogous to the synthetic route disclosed in WO2004/111057 from compounds of formula (II) and aminoethanol. Typically, this reaction is carried out using a coupling reagent such as 1-ethyl-3-(3-dimethylaminopropyl)-carbodiimide (EDC) or 2-(7-aza-1H-benztriazole-1-yl)-1,1,3,3-tetramethyluronium hexafluorophosphate (HATU) utilising standard methods familiar to those skilled in the art such as reaction in solvent such as tetrahydrofuran, acetonitrile or dimethylformamide at a range of temperatures from ambient to reflux temperature. Alternatively, compounds of formula (I) may be prepared from compounds of formula (III) by displacement of the 2-chloro substituent with a compound of formula (IX) in the presence of a base such as N,N-diisopropylethylamine and a solvent such as N-methyl pyrrolidinone with conventional heating or microwave irradiation.

(II)

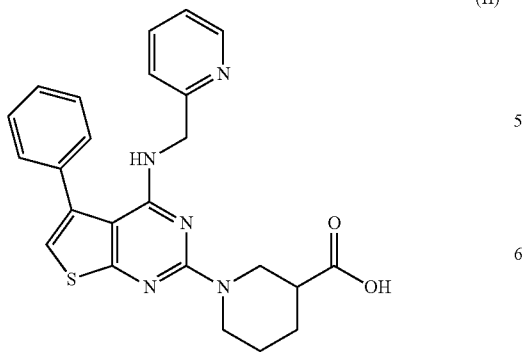

Compounds of formula (II) may be prepared from a compound of formula (III) by displacement of the 2-chloro substituent with commercially available nipecotic acid, in the presence of a base such as N,N-diisopropylethylamine and a solvent such as N-methyl pyrrolidinone with conventional heating or microwave irradiation.

(III)

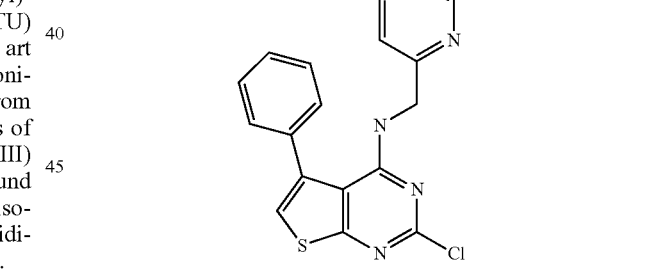

Compounds of formula (III) are readily synthesised from compounds of formula (IV) by a nucleophilic substitution reaction with 2-aminomethylpyridine, optionally in the presence of a solvent and a base, and optionally at elevated temperature or with microwave irradiation. Preferably the solvent (if present) is an alcohol, preferably ethanol and the base is a hindered nitrogen base such as triethylamine. The reaction is carried out at ambient temperatures.

(IV)

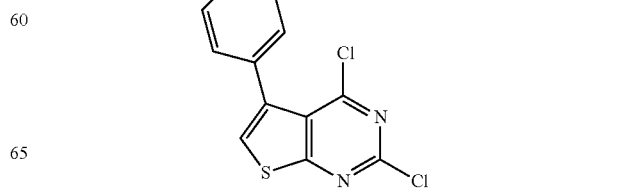

A compound of formula (IV) may be synthesised by reaction of a compound of formula (V) with a chlorinating reagent such as phenylphosphonic dichloride or phosphorous oxychloride.

(V)

Compounds of formula (V) may be synthesised by the reaction of a compound of formula (VI) with an alkali metal cyanate, preferably potassium cyanate.

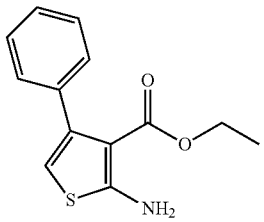
(VI)

A compound of formula (VI) can be prepared by the "Gewald reaction" in which a compound of formula (VII) is reacted under basic conditions and in a suitable solvent such as ethanol, with powdered sulphur. Preferably the base is diisopropylethylamine (Hünig's base) and the solvent may be an alcohol, preferably ethanol, and the reaction is carried out between 25 and 65° C.

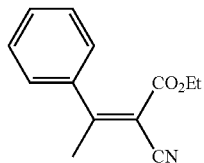
(VII)

Compounds of formula (VII) can be prepared by the Knoevenagel condensation reaction by heating compound of formula (VIII) with ethylcyanoacetate ($NCCH_2CO_2Et$) in the presence of an acid and ammonium acetate in a suitable solvent such as toluene, optionally with azeotropic water removal. Preferably the acid is acetic acid. This gives the alkylidene cyano ester as a pair of (E and Z) geometric isomers.

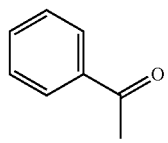
(VIII)

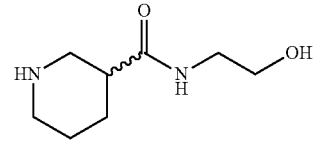
(IX)

Compound of formula (IX) may be prepared from compound of formula (X) by hydrolysis of the t-butyl carbamate (BOC) protecting group with a strong acid in a solvent such as dichloromethane. Typically the acid is trifluoroacetic acid.

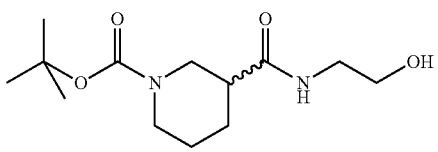
(X)

Compound of formula (X) may be prepared from a compound of formula (XI) and aminoethanol. Typically, this reaction is carried out using a coupling reagent such as 1-ethyl-3-(3-dimethylaminopropyl)-carbodiimide (EDC) or 2-(7-aza-1H-benztriazole-1-yl)-1,1,3,3-tetramethyluronium hexafluorophosphate (HATU) utilising standard methods familiar to those skilled in the art such as reaction in solvent such as tetrahydrofuran, acetonitrile or dimethylformamide at a range of temperatures from ambient to reflux temperature.

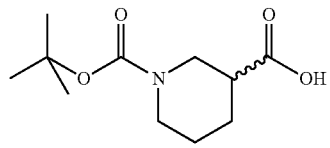
(XI)

Pharmaceutical Compositions

As discussed herein, the compounds of the invention are useful in the treatment of various conditions. Thus, the second aspect of the invention provides a pharmaceutical composition or formulation comprising at least one compound of the invention and optionally one or more pharmaceutically acceptable excipients.

Typical pharmaceutically acceptable excipients include:
diluents, e.g. lactose, dextrose, sucrose, mannitol, sorbitol, cellulose and/or glycine;
lubricants, e.g. silica, talcum, stearic acid, its magnesium or calcium salt and/or polyethyleneglycol;
binders, e.g. magnesium aluminum silicate, starch paste, gelatin, tragacanth, methylcellulose, sodium carboxymethylcellulose and/or polyvinylpyrrolidone;
disintegrants, e.g. starches, agar, alginic acid or its sodium salt, or effervescent mixtures; and/or
absorbants, colorants, and/or sweeteners.

The compositions of the invention may be presented in unit dose forms containing a predetermined amount of each active ingredient per dose. Such a unit may be adapted to provide 5-100 mg/day of the compound, preferably either 5-15 mg/day, 10-30 mg/day, 25-50 mg/day 40-80 mg/day or 60-100 mg/day. For compounds of the invention, doses in the range 100-1000 mg/day are provided, preferably either 100-

400 mg/day, 300-600 mg/day or 500-1000 mg/day. Such doses can be provided in a single dose or as a number of discrete doses. The ultimate dose will depend on the condition being treated, the route of administration and the age, weight and condition of the patient and will be at the doctor's discretion.

The compositions of the invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For applications to the eye or other external tissues, for example the mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

MODES FOR CARRYING OUT THE INVENTION

The following protocols describe preparation of:—
1. racemate made using "convergent route" (Examples 1 to 6)
2. enantiomers made using "convergent route" (Examples 1 to 5 and 7 to 12)
3. enantiomers made using "linear route" (Examples 1 to 5 and 13 to 16)

Synthesis and Determination of Enantiomers

The desired enantiomerically pure compound was obtained by the careful selection of reagents and the use of appropriate experimental conditions and sequence in particular with regard to steps forming the chiral center and subsequent reaction. It was determined during the course of synthesis that the "linear route" was less prone to racemisation as the final amide forming bond could be carried out at lower temperature as opposed to the "convergent route" which provided better yields but with detectable racemisation.

For the "linear route", pure enantiomers of the nipecotic acid were obtained by classical resolution of cheap commercially available racemic nipecotic acid using 1-(S)-camphor sulfonic acid as the resolving agent, determining ee analysis after forming a BOC derivative of a sample.

The enantiomeric purity was determined by Chiral HPLC.

Analytical Methods

Proton magnetic resonance ($^1$H NMR) spectra were recorded on a Varian 400 MHz Mercury Plus spectrometer. All spectra were determined in dmso-d6 unless otherwise stated and chemical shifts are reported in (sigma) units downfield from the internal standard tetramethylsilane (TMS) and interproton coupling constants are reported in Hertz (Hz), splitting paterns are designated as follows: s, singlet; d, doublet; t, triplet; q, quartet; m, multiplet; br, broad peak; dd, doublet of doublet; dt, doublet of triplet; bs, broad singlet; dq, doublet of quartet.

IR spectra were determined on a Perkin Elmer Spectrum One instrument.

Mass spectra were determined on an Agilent 6310 Ion trap instrument.

HPLC analysis (method (a)) was carried out on a Waters 2695 system using ZORBAX SB C-18 (4.6×50 mm) column; Mobile phase: A: 0.05% TFA (AQ,) B: 0.05% TFA (MeCN); T % B: 0/20, 5/90, 8/90, 8.1/20; flow rate 1.0 mL/min;

Chiral column: Chiralpak IC (4.6×250 mm) 5 u, mobile phase: A: Hexane, B: EtOH (70:30); flow rate 0.8 ml/min run over 40 minutes.

Melting points were determined on an EX-Melt instrument (Model: MPA120).

Alternatively, HPLC analysis (method (b)) was carried out with: Waters 616 fluid handling system, Waters 996 photodiode array detector.

Chiral column: Daicel Chiralpak AD-H (Chiral technologies) reporting chiral purity at 244 nm; mobile phase 80% Hexanes:20% EtOH; flow rate 0.8 ml/min; temp 40° C.

Mass spectra were determined on an Agilent 1100 series instrument (Model: G1946C).

Using the information outlined herein the following compounds can be synthesised which are given by way of example only. The pharmacological profile of compounds of the present invention can readily be assessed by those skilled in the art using routine experimentation, such as procedures and techniques illustrated herein and described in detail in Ford et al., 2002.

Example 1

(Z)-2-Cyano-3-phenyl-but-2-enoic acid ethyl ester (VII)

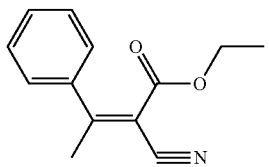 [SMILES: CCOC(=O)/C(C#N)=C(/C)c1ccccc1]

A stirred mixture of acetophenone (VIII) (180 g, 1.5 mol), ethyl cyanoacetate (170 g, 1.3 mol), ammonium acetate (23.1 g), acetic acid (72 g) and toluene (300 ml) was heated under reflux for 18 hours while water was removed from the reaction by azeotropic distillation. The mixture was allowed to cool to ambient temperature, toluene (100 ml) was added, then the mixture was washed with water (3×100 ml). The combined aqueous washings were shaken with toluene (50 ml), then the combined toluene solutions were dried over magnesium sulphate, filtered and the solvent was removed in vacuo. The residual oil was distilled under reduced pressure to give 2-cyano-3-phenyl-but-2-enoic acid ethyl ester as an oil (309 g) which was used without further purification.

Example 2

2-Amino-4-phenyl-thiophene-3-carboxylic acid ethyl ester (VI)

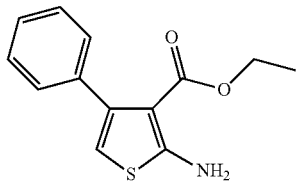 [SMILES: CCOC(=O)c1c(-c2ccccc2)csc1N]

2-Cyano-3-phenyl-but-2-enoic acid ethyl ester (513.25 g, 2.3 mol) was added at ambient temperature to a vigorously-stirred suspension of powdered sulfur (76 g, 2.3 mol) in ethanol (500 ml). Diethylamine (200 ml) was added in portions over 20 minutes, during which time the temperature of the reaction rose to 62° C. The mixture was allowed to cool to 36° C., then it was heated to 50° C. and stirring at that temperature was continued for 1 hr. After this time, stirring was discontinued, the hot solution was removed by decantation from unreacted sulfur, then it was allowed to cool to ambient temperature. The resulting solid was collected by filtration, washed with a little cold ethanol and dried in vacuo to give 2-amino-4-phenylthiophene-3-carboxylic acid ethyl ester as an orange solid (195 g) which was used without further purification.

Example 3

5-Phenyl-1H-thieno[2,3-d]pyrimidine-2,4-dione (V)

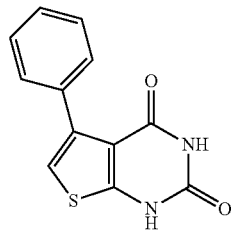 [SMILES: O=c1[nH]c(=O)c2c(-c3ccccc3)csc2[nH]1]

2-Amino-4-phenyl-thiophene-3-carboxylic acid ethyl ester (2.0 g, 8.1 mmol), and Potassium Cyanate (Aldrich, 2.0 g, 24.3 mmol) were added to glacial acetic acid (VWR, 20 ml) and stirred at ambient temperature for 18 h. The reaction was diluted with water (50 ml) and the resultant precipitate filtered, washed with water and dried to a damp cake. The solid was suspended in water (100 ml) and made alkaline to pH 12-14 by the addition of concentrated sodium hydroxide. The resultant suspension was heated at 100° C. for 2 h with stirring, then cooled to ambient temperature and acidified by the addition of glacial acetic acid. The resulting solid was collected by filtration, washed with water and dried in vacuo at 40° C. to give 5-Phenyl-1H-thieno[2,3-d]pyrimidine-2,4-dione as a white solid. Yield=(1.1 g, 56%).

Example 4

2,4-Dichloro-5-phenyl-thieno[2,3-d]pyrimidine (IV)

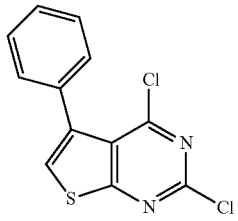 [SMILES: Clc1nc(Cl)c2c(-c3ccccc3)csc2n1]

A stirred mixture of 5-Phenyl-1H-thieno[2,3-d]pyrimidine-2,4-dione (1.07 g, 4.39 mmol) and phenyl phosphonic dichloride (Aldrich, 10 ml, excess) was heated at 150° C. for 7 h then allowed to stand at ambient temperature for 18 hrs. The resulting dark solution was poured into ice-water and extracted with DCM (3×150 ml). The combined extracts were washed with saturated sodium hydrogen carbonate solution (150 ml) and dried (MgSO$_4$). The solvent was removed in vacuo and the oily residue triturated with 40-60° C. petroleum ether to give 2,4-Dichloro-5-phenyl-thieno[2,3-d]pyrimidine as a pale yellow solid. Yield=(0.82 g, 66%).

Example 5

(2-Chloro-5-phenyl-thieno[2,3-d]pyrimidin-4-yl)-pyridin-2-ylmethyl-amine (III)

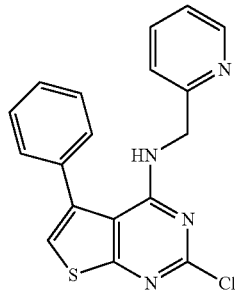 [SMILES: Clc1nc(NCc2ccccn2)c2c(-c3ccccc3)csc2n1]

A mixture of 2,4-Dichloro-5-phenyl-thieno[2,3-d]pyrimidine (1.77 g, 6.3 mmol), 2-aminomethylpyridine (Aldrich, 782 μl, 7.6 mmol), and triethylamine (VWR, 1.06 ml, 7.63 mmol) were refluxed in ethanol (30 ml) for 3 hrs. On cooling, the reaction was poured into water (300 ml) and stirred for 1 hr. The resulting precipitate was filtered, washed with water (2×30 ml) and dried under vacuum at 40° C. to give (2-Chloro-5-phenyl-thieno[2,3-d]pyrimidin-4-yl)-pyridin-2-ylmethyl-amine as a pale-yellow solid. Yield=(1.55 g, 70%).

Racemate—Convergent Route

Example 6

(Racemic) 1-{5-Phenyl-4-[(pyridin-2-ylmethyl)-amino]-thieno[2,3-d]pyrimidin-2-yl}-piperidine-3carboxylic acid (2-hydroxy-ethyl)-amide (Ia)

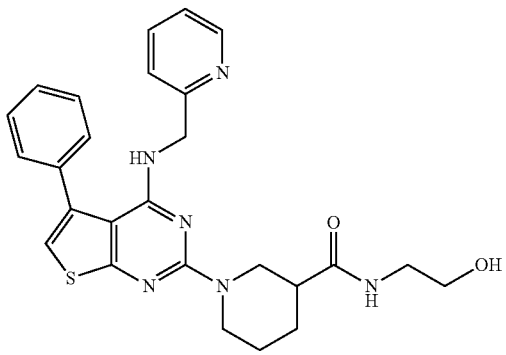 [SMILES: O=C(NCCO)C1CCCN(c2nc(NCc3ccccn3)c3c(-c4ccccc4)csc3n2)C1]

(2-Chloro-5-phenyl-thieno[2,3-d]pyrimidin-4-yl)-pyridin-2-ylmethyl-amine (44 mg, 0.124 mmol), Piperidine-3-carboxylic acid(2-hydroxyethyl)amide (Fluorochem, 32 mg, 0.188 mmol, 1.5 eq) and N,N-diisopropylethylamine (Aldrich, 0.188 mmol) were dissolved in N-Methyl Pyrrolidinone (1.5 ml) in a Biotage microwave tube and heated to 200° C. and maintained at this temperature for 30 min. On cooling, the solvents were removed in vacuo. The residue was triturated with DCM (2×10 ml) and the extracts combined, concentrated and purified by prep TLC (eluent 10% MeOH/DCM) to give the product as a yellow oil, which slowly solidified on standing to a waxy solid. The waxy solid may be converted to a free-flowing powder by stirring in diethyl ether for 1-2 h (0.5 g in 10 ml). Yield=18.3 mg (30%)

Enantiomers—Convergent Route

Example 7

(S)-3-(2-Hydroxy-ethylcarbamoyl)-piperidine-1-carboxylic acid tert-butyl ester

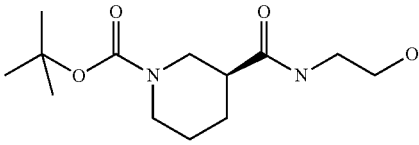 [SMILES: CC(C)(C)OC(=O)N1CCC[C@H](C(=O)NCCO)C1]

(S)-Piperidine-1,3-dicarboxylic acid 1-tert-butyl ester (500 mg, 2.2 mmol), HATU (833 mg, 2.2 mmol) and Di-isopropylethylamine (761 μL, 4.4 mmol) were stirred in dry DCM (10 ml) in an ice bath for 5 min, then at room temperature for 5 min. Ethanolamine (198 μL, 3.28 mmol) was added and the reaction stirred at room temperature for 3 hrs. The reaction was diluted with DCM (40 ml), washed with water (50 ml), the DCM layer separated and dried (MgSO$_4$) and concentrated. The residue was columned on silica (20 g isolute). Eluting: MeOH/DCM 0-5% 5 CV, MeOH/DCM 5%-5% 10 CV, MeOH/DCM 5-10% 5 CV. TLC visualized with KMnO$_4$. This yielded the product as a clear oil (327 mg).

Similarly was prepared:

Example 8

(R)-3-(2-Hydroxy-ethylcarbamoyl)-piperidine-1-carboxylic acid tert-butyl ester

Example 9

(S)-Piperidine-3-carboxylic acid (2-hydroxy-ethyl)-amide

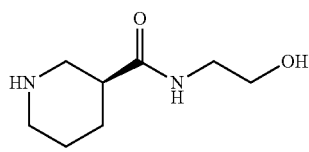 [SMILES: O=C(NCCO)[C@H]1CCCNC1]

The product of the above reaction was stirred in 1:1 TFA/DCM for 2 hrs then concentrated in vacuo to an oil. This was dissolved in MeOH (5 ml) and loaded onto a 5 g SCX cartridge. The cartridge was washed with MeOH (10 ml), then the product eluted with 2M NH$_3$/MeOH (10 ml). The fraction was concentrated to give a white solid. Yield=260 mg.

Similarly was prepared:

Example 10

(R)-Piperidine-3-carboxylic acid (2-hydroxy-ethyl)-amide

Example 11

(S)-1-{5-Phenyl-4-[(pyridin-2-ylmethyl)-amino]-thieno[2,3-d]pyrimidin-2-yl}-piperidine-3-carboxylic acid (2-hydroxy-ethyl)-amide (Ib)

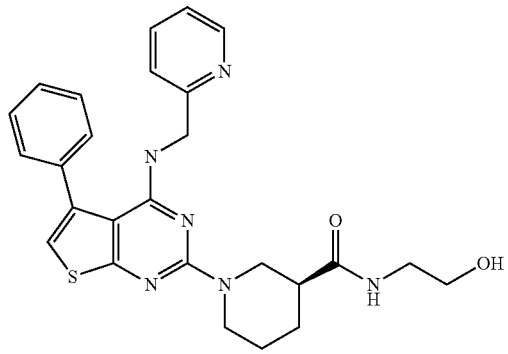 [SMILES: O=C(NCCO)[C@H]1CCCN(c2nc(NCc3ccccn3)c3c(-c4ccccc4)csc3n2)C1]

(S)-Piperidine-3-carboxylic acid (2-hydroxy-ethyl)-amide was reacted with (2-Chloro-5-phenyl-thieno[2,3-d]pyrimidin-4-yl)-pyridin-2-ylmethyl-amine as in Example 6 above to give (S)-1-{5-Phenyl-4-[(pyridin-2-ylmethyl)-amino]-thieno[2,3-d]pyrimidin-2-yl}-piperidine-3-carboxylic acid (2-hydroxy-ethyl)-amide as a yellow foam (188 mg).

Similarly was prepared:

Example 12

(R)-1-{5-Phenyl-4-[(pyridin-2-ylmethyl)-amino]-thieno[2,3-d]pyrimidin-2-yl}-piperidine-3-carboxylic acid (2-hydroxy-ethyl)-amide (Ic)

Enantiomers—Linear Route Via

Example 13

(S)-Nipecotic Acid-(S)-Camphorsulfonate Salt

Chiral Resolution of (S) Nipecotic Acid from Commercial Racemic Mixture

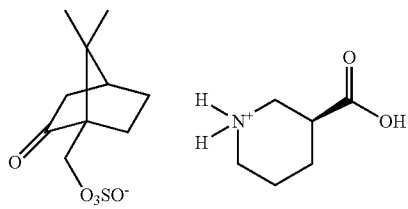

To a solution of (S)-camphorsulfonic acid (18 kg, 77 mol) in acetone (127 kg) at 55-58° C., a solution of (R,S)-nipecotic acid (10 kg, 77 mol) in water (20 kg) was quickly charged. The mixture was maintained at 55-58° C. until all solids were dissolved. The solution was slowly cooled to 20-25° C. to precipitate the salt, then stirred overnight, and isolated. To further increase the diastereomeric purity, the resulting salt was re-crystallized from acetone (16 kg) and water (4 kg) at 55-58° C. Again, the hot solution was cooled to 20-25° C., stirred overnight, and isolated to give the purified (S)-nipecotic acid-(S)-camphorsulfonate salt (14 kg).

Example 14

(S)-Piperidine-3-carboxylic acid hydrochloride

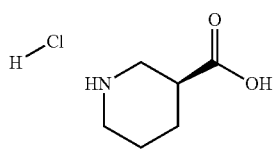

(S)-Piperidine-1,3-dicarboxylic acid 1-tert-butyl ester (20 kg, 87.2 mol) was slurried in acetic acid (189 kg) and cooled to 15° C. An excess of hydrogen chloride gas (9.6 kg) was charged and stirred for ~4 hours to complete deprotection. The slurry was isolated and filter-cake rinsed with acetic acid (2×31.5 kg). The filter cake was then vacuum dried to obtain product (14.4 kg).

Example 15

(S)-1-{5-Phenyl-4-[(pyridin-2-ylmethyl)-amino]-thieno[2,3-d]pyrimidin-2-yl}-piperidine-3-carboxylic acid

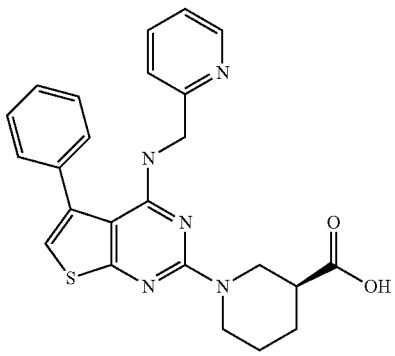 [SMILES: O=C(O)[C@H]1CCCN(c2nc(NCc3ccccn3)c3c(-c4ccccc4)csc3n2)C1]

(2-Chloro-5-phenyl-thieno[2,3-d]pyrimidin-4-yl)-pyridin-2-ylmethyl-amine (5.9 kg, 16.7 mol) and (S)-nipecotic acid hydrochloride (4.15 kg, 25.1 mol) were dissolved in butyrolnitrile (13.9 kg). An excess of diisopropylethylamine (8.6 kg, 66.9 mol) was added and the mixture heated to 110° C. for 24 to 48 hours to complete reaction. With coupling complete (<2% nipecotic acid remaining), the reaction was cooled to room temperature and water (29 kg) was charged. The mixture pH was adjusted to ~10 with 25% aqueous sodium hydroxide (4.5 L) and the layers separated. The product aqueous layer was extracted twice with ethyl acetate (15.9 L) then methylene chloride (23.5 kg) was added to the aqueous layer and the pH adjusted to ~2.5 with concentrated hydrochloric acid (6.3 kg). The layers were separated and the aqueous layer re-extracted with methylene chloride (2×15.7 kg). The methylene chloride layers were combined and washed with water (18 kg) then dried over sodium sulfate (5.9 kg) and product solution was held for processing in next step (Example 16).

Example 16

(S)-1-{5-Phenyl-4-[(pyridin-2-ylmethyl)-amino]-thieno[2,3-d]pyrimidin-2-yl}-piperidine-3-carboxylic acid (2-hydroxy-ethyl)-amide (Ib)

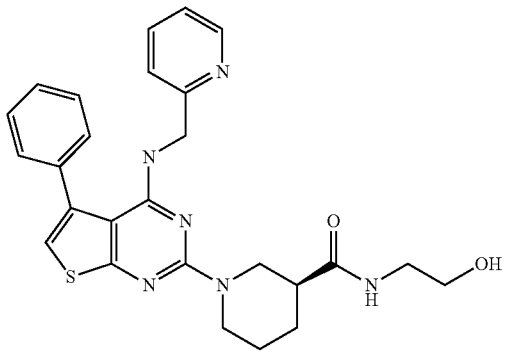 [SMILES: O=C(NCCO)[C@H]1CCCN(c2nc(NCc3ccccn3)c3c(-c4ccccc4)csc3n2)C1]

(S)-1-{5-Phenyl-4-[(pyridin-2-ylmethyl)-amino]-thieno[2,3-d]pyrimidin-2-yl}-piperidine-3-carboxylic acid solution (7.4 kg, 16.63 mol) (from Example 15) was cooled to 0° C. and diisopropylamine (4.51 kg, 35 mol) and ethanolamine (2.03 kg, 33.3 mol) were added. Maintaining the reaction temperature below 10° C., bezotriazolyl tetramethyluronium-BF4 (TBTU) (5.9 kg, 18.3 mol) was charged in portions then stirred at ~5 C until the coupling was complete. The reaction solution was then filtered to remove TBTU salts and washed with water (22.2 L), followed by two washes with citric acid/sodium hydroxide buffer aqueous solution (pH~5) (2.88 kg, 15 mol), and finally with a brine solution (4 L). Subsequently, the mixture was charged with butyronitrile (17.4 L) and partially stripped to precipitate the diastereomeric product. The slurry was filtered to remove diastereoisomer and the filtrates stripped further to ~½ volume. To the mix heptanes (30.4 L) was charged to precipitate product and the slurry cooled to room temperature. The slurry was filtered, rinsed with heptanes (10.1 L), and vacuum dried to obtain product (4.1 kg).

(R)-1-{5-Phenyl-4-[(pyridin-2-ylmethyl)-amino]-thieno[2,3-d]pyrimidin-2-yl}-piperidine-3-carboxylic acid (2-hydroxy-ethyl)-amide (Ic) may be prepared according to a route analogous to Examples 13 to 16.

Example 17

Analytical data for the compounds represented by the above examples are shown in the table below.

| Ex | NMR spectrum $^1$H (400 MHz; dmso-d6) | HPLC (RT) mins | Mass Spec (M$^{+1}$) | Chiral HPLC (method (a)) | MP (° C.) | FT-IR λmax (cm$^{-1}$) |
|---|---|---|---|---|---|---|
| 2 | 0.91 (3H, t), 3.96 (2H, q), 6.15 (1H, s) 7.3 (5H, m) | 4.8 | 248 (99.5%) | | | |
| 3 | 6.67 (1H, s), 7.3 (3H, m), 7.47 (2H, m) | (uplc) | 245 (98.9%) | | | |
| 4 | 7.51 (5H, m), 7.99 (1H, s) | (uplc) | 282 (92% | | | |
| 5 | 4.64 (2H, s), 7.07 (1H, m), 7.23 (1H, m), 7.4 (1H, d), 7.55 (6H, m), 7.75 (1H, dt), 8.21 (1H, m) | (uplc 1.75) | 353 (97.6%) | | | |
| 6 | 1.3 (1H, m), 1.6 (2H, m), 1.8 (1H, m), 2.3 (1H, m), 2.8 (2H, m), 3.1 (2H, m), 3.4 (2H, m), 4.6 (5H, m), 6.3 (1H, m), 6.95 (1H, s), 7.2-7.3 (2H, m), 7.5 (5H, m), 7.7 (1H, m), 7.9 (1H, m), 8.3 (1H, m) | 2.67 (uplc 0.91) | 489 (99.8%) | | 190-194 | 3338, 3298, 3098, 3009, 2931, 2847, 1642, 1556, 1517, 1504, 1484, 1438, 1386, 1321, 1300, 1255, 1220, 1203, 1139, 1062 |
| 11 (S) | 1.3 (1H, m), 1.6 (2H, m), 1.8 (1H, m), 2.3 (1H, m), 2.8 (2H, m), 3.2 (2H, m), 3.4 (2H, m), 4.6 (5H, m), 6.3 (1H, t), 6.95 (1H, s), 7.2 (1H, dd), 7.3 (1H, d), 7.5 (5H, m), 7.7 (1H, dd), 7.9 (1H, m), 8.3 (1H, m) | — | 489.3 | 98.3% RT = 18.4 min | 61-65 | 3426, 3357, 1649 |
| 12 (R) | 1.3 (1H, m), 1.6 (2H, m), 1.8 (1H, m), 2.3 (1H, m), 2.8 (2H, m), 3.2 (2H, m), 3.4 (2H, m), 4.6 (5H, m), 6.3 (1H, t), 6.95 (1H, s), 7.2 (1H, dd), 7.3 (1H, d), 7.5 (5H, m), 7.7 (1H, dd), 7.9 (1H, m), 8.3 (1H, m) | — | 489.3 | 97.6% RT = 14.87 MIN | 71-76 | 3425, 3352, 1649 |

Example 18

Kv1.5 Electrophysiology Method

The ability of the compounds of the invention to inhibit the Kv1.5 potassium channel was measured in an electrophysiology experiment, using recombinant cells expressing the channel of interest in a whole cell patch clamp experiment.

The external bathing solution contained (in mM): 150 NaCl, 10 KCl, 3 MgCl$_2$, 1 CaCl$_2$, HEPES, pH 7.4. Patch pipettes were filled with an electrode solution of composition (in mM): 160 KCl, 0.5 MgCl$_2$, 10 HEPES, 1 EGTA, pH 7.2 with KOH.

Compounds were dissolved in DMSO (100%) and freshly made up in the external bather at the desired concentration (final DMSO concentration=0.1%). All experiments were conducted at room temperature.

For whole-cell patch-clamp studies cells (CHO stably transfected with hKv1.5) were seeded onto glass coverslips before recordings were made. Cells were seeded in sterile 30 mm Petri dishes at a density to enable isolated cells to be selected for patch clamp experiments. The dishes were stored in a humidified, gassed (5% $CO_2$) incubator at 37° C. until use.

Whole-cell patch-clamp recordings of membrane currents were made following gigaohm seal formation between the patch electrode and the cell using HEKA EPC-9/10 amplifiers controlled by Pulse Software (Ver8.5x/8.6x, HEKA, Germany). Coverslips seeded with cells were placed in a recording chamber mounted on the stage of an inverted microscope. During the experiment the cell of interest was continuously superfused with bather solution delivered via a cannula placed in close proximity to the cell to enable control of the extracellular solution environment. Only those cells with a current>500 pA were used for experiments. During experiments total series resistance did not exceed 10 MΩ and was compensated by a minimum of 70%. Leak subtraction was performed online using a P/n protocol in Pulse.

Electrophysiology voltage-step protocols and analysis of data was performed as follows. Data was sampled at 5 kHz, and filtered with a −3 dB bandwidth of 2.5 kHz. Cells were held at a voltage of −80 mV. Currents were evoked by a depolarising voltage step to 0 mV (900 ms) before repolarisation first to −40 mV (100 ms) before returning to −80 mV. The command waveform as repeatedly applied every 5 s throughout the experiment. Mean currents during 75-95% of the depolarising step to 0 mV were analysed using Pulsefit software (v8.x, HEKA, Germany). The voltage protocol was applied a achieve a stable current baseline in bather before the test substance was superfused via the cannula; fluid exchange took approximately 15 s. The test substance was allowed to equilibrate during which time voltage protocol was repeatedly applied and recorded. Percentage inhibition of the current in the presence of test substance was calculated relative to the control pre-drug value.

|  | Compound | Kv1.5 $IC_{50}$ (nM) |
|---|---|---|
| Racemate | 1-{5-Phenyl-4-[(pyridin-2-ylmethyl)-amino]-thieno[2,3-d]pyrimidin-2-yl}-piperidine-3 carboxylic acid (2-hydroxy-ethyl)-amide | 9 |
| (S) enantiomer (Ib) | (S)-1-{5-Phenyl-4-[(pyridin-2-ylmethyl)-amino]-thieno[2,3-d]pyrimidin-2-yl}-piperidine-3-carboxylic acid (2-hydroxy-ethyl)-amide | 27 |
| (R) enantiomer (Ic) | (R)-1-{5-Phenyl-4-[(pyridin-2-ylmethyl)-amino]-thieno[2,3-d]pyrimidin-2-yl}-piperidine-3-carboxylic acid (2-hydroxy-ethyl)-amide | 5 |

Example 19

Selectivity screening

A compound of the invention and a comparative compound were screened in the following assays:
1. Nav1.5; screened on the Sophion QPatch using CHO cells expressing hNav1.5 currents, stably transfected with heterologous hNav1.5 cDNA.
2. Kv4.3; screened by manual whole cell patch clamp using CHO cells expressing hKv4.3 currents, stably transfected with heterologous Kv4.3 cDNA.
3. hERG; screened by manual whole cell patch clamp using HEK293 cells expressing hERG currents, stably transfected with heterologous hERG cDNA.
4. Kir3.1/3.4; screened by manual whole cell patch clamp using HEK293 cells expressing rKir3.1/3.4 currents, stably transfected with heterologous rKir3.1 and rKir3.4 cDNA.
5. KCNQ1; screened by manual whole cell patch clamp using CHO cells expressing hKCNQ1/hmink currents, stably transfected with heterologous hKCNQ1/hmink cDNA.
6. Kir2.1; screened by manual whole cell patch clamp using HEK293 cells expressing hKir21. currents, stably transfected with heterologous hKir2.1 cDNA.
7. Cav1.2; screened using GH3 cells or HEK293 cells expressing hCav1.2 currents, stably transfected with heterologous hCav1.2 cDNA.

The selectivity ratios for Kv1.5 as compared to the above ion channels are shown below:

| Ion Channel | Compound of the invention | Comparative compound |
|---|---|---|
| Nav1.5 | >350x | ~120x |
| Kv4.3 | ~500x | 17x |
| hERG | ~275x | 54x |
| Kir3.1/3.4 | ~265x | ~42x |
| KCNQ1 | ~1200x | ~300x |
| Kir2.1 | >400x | >1245x |
| Cav1.2 | >1200x | >1245x |

Example 20

Inhibition of the $I_{Kur}$ Current in Dissociated Human Atrial Myocytes

Isolation of Human Atrial Myocytes

Specimens of human atrial appendage (either right or left) were obtained from patients undergoing a range of cardiac surgical procedures. Tissue was obtained from consenting patients from Papworth Hospital NHS Trust, Cambs. UK. following approval from the Local Research Ethical Approval Committee. The mechano-enzymatic isolation of myocytes was performed using a modified protocol as described by Wang et al. (1993) and Dobrev et al. (2005). Isolated myocytes were suspended in a modified 'Krafte-brühe' (KB) solution until use.

Recording System

Myocytes were placed into a small-volume recording chamber with a glass-coverslip base, mounted on the stage of an inverted microscope. During the experiment, the cell of interest was constantly superfused with bather solution delivered via a cannula placed in close proximity to the cell to enable control of the extracellular solution environment. Whole-cell patch-clamp recordings of membrane currents were made using a HEKA EPC-9/10 amplifier following Gigaohm seal formation between the patch electrode and the myocyte. Glass patch-pipettes were pulled from borosilicate glass. Only rod-shaped, striated myocytes were selected for use. Capacitance and series resistance were compensated using Pulse software. Voltage-clamp commands were generated using Pulse software and data were recorded onto the hard disk of a PC. Leak subtraction was not performed and cells with significant leak were rejected. Experiments were performed at room temperature. To minimise contamination from other ionic currents, experimental solutions contained 10 mM tetraethylammonium chloride ($I_K$), 100 nM atropine ($I_{K,ACh}$), 200 μM $CdCl_2$ ($I_{Ca,L}$; and $I_{Cl,Ca}$), 0.5 mM $BaCl_2$ ($I_{KI}$ and $I_{KACh}$). Blockers were used at a concentration that would not be expected to affect $I_{Kur}$. The sodium current ($I_{Na}$) was suppressed by using a choline chloride based bather. Depolarising voltage-step were applied every 10 s to elicit an outward potassium current composed of a transient and sustained component. The sustained current sensitive to 300 µM 4-AP was defined as the ultra-rapid delayed rectifier current, $I_{Kur}$.

| Ionic current | Compound of the invention | Comparative compound |
|---|---|---|
| $hI_{Kur}$ | 11 nM | 154 nM |

Abbreviations
HGNC HUGO Gene Nomenclature Committee
$Kv_{(ur)}$ Cardiac Ultrarapid Delayed Rectifier
CHO Chinese Hamster Ovary Cells
$IP_3$ Inositol Triphosphate
CRAC $Ca^{2+}$-Release-Activated-$Ca^{2+}$ Current
DMEM Dulbecco's Modified Eagle media
DMSO Dimethyl sulphoxide
FCS Fetal Calf Serum
EBSS Earls Balanced Salt Solution
WCPC Whole-Cell Patch-Clamp
HEK293 Human Embryonic Kidney 293 Cells

REFERENCES

Herbert, "General principles of the structure of ion channels", Am. J. Med, 104, 87-98, 1998.
Armstrong & Hille, "Voltage-gated ion channels and electrical excitability", Neuron, 20, 371-380, 1998.
Gutman G A, Chandy K G, Adelman J P, Aiyar J, Bayliss D A, Clapham D E, Covarriubias M, Desir G V, Furuichi K, Ganetzky B, Garcia M L, Grissmer S, Jan L Y, Karschin A, Kim D, Kuperschmidt S, Kurachi Y, Lazdunski M, Lesage F, Lester H A, McKinnon D, Nichols C G, O'Kelly I, Robbins J, Robertson G A, Rudy B, Sanguinetti M, Seino S, Stuehmer W, Tamkun M M, Vandenberg C A, Wei A, Wulff H, Wymore R S International Union of Pharmacology. XLI. Compendium of voltage-gated ion channels: potassium channels. Pharmacol Rev. 2003 December; 55(4):583-6.
Shieh et al. "Potassium channels: molecular defects, diseases, and therapeutic opportunities", Pharmacol Rev, 52(4), 557-594, 2000.
Ford et al. "Potassium Channels: Gene Family, Therapeutic Relevance, High-Throughput Screening Technologies and Drug Discovery", Prog Drug Res, 58, 133-168, 2002.
Marban "Cardiac channelopalthies", Nature, 415, 213-218, 213-218, 2002.
Brendel and Peukert 'Blockers of the Kv1.5 Channel for the Treatment of Atrial Arrhythmias', Expert Opinion in Therapeutic Patents, 12 (11), 1589-1598 (2002).
Wang et al., "Sustained depolarization-induced outward current in human atrial myocytes. Evidence for a novel delayed rectifier K+ current similar to Kv1.5 cloned channel currents", Circ Res, 73, 1061-1076, 1993.
Fedida et al., "Identity of a novel delayed rectifier current from human heart with a cloned K+ channel current", Circ Res, 73, 210-216, 1993.
Feng et al., "Antisense oligodeoxynucleotides directed against Kv1.5 mRNA specifically inhibit ultrarapid delayed rectifier K+ current in cultured adult human atrial myocytes", Circ Res, 80, 572-579, 1997.
Amos et al., "Differences between outward currents of human atrial and subepicardial ventricular myocytes", J Physiol, 491, 31-50, 1996.
Li et al., "Evidence for two components of delayed rectifier K+ current in human ventricular myocytes", Circ Res, 78, 689-696, 1996.

Nattel, 'Therapeutic implications of atrial fibrillation mechanisms: can mechanistic insights be used to improve A F management?' Cardiovascular Research, Volume 54, Issue 2, 347-360, 2002.
Courtemanche et al., "Ionic targets for drug therapy and atrial fibrillation-induced electrical remodeling: insights from a mathematical model", Cardiovasc Res, 42(2), 477-489, 1999.
Nattel et al., "Cardiac ultrarapid delayed rectifiers: a novel potassium current family of functional similarity and molecular diversity", Cell Physiol Biochem, 9(4-5), 217-226, 1999.
Knobloch K, Brendel J, Peukert S, Rosenstein B, Busch A E, Wirth K J. Electrophysiological and antiarrhythmic effects of the novel I(Kur) channel blockers, S9947 and S20951, on left vs. right pig atrium in vivo in comparison with the I(Kr) blockers dofetilide, azimilide, d,l-sotalol and ibutilide. Naunyn Schmiedebergs Arch Pharmacol. 2002 November; 366(5):482-7.
Wirth K J, Paehler T, Rosenstein B, Knobloch K, Maier T, Frenzel J, Brendel J, Busch A E, Bleich M. Atrial effects of the novel K(+)-channel-blocker AVE0118 in anesthetized pigs. Cardiovasc Res. November 1; 60(2):298-306, 2003.
Colatsky et al., "Channel specificity in antiarrhythmic drug action. Mechanism of potassium channel block and its role in suppressing and aggravating cardiac arrhythmias", Circulation, 82(6), 2235-2242, 1990.
Feng et al., "Effects of class III antiarrhythmic drugs on transient outward and ultra-rapid delayed rectifier currents in human atrial myocytes", J Pharmacol Exp Ther, 281(1), 384-392, 1997.
Wang et al., "Effects of flecainide, quinidine, and 4-aminopyridine on transient outward and ultrarapid delayed rectifier currents in human atrial myocytes", J Pharmacol, 272(1), 184-196, 1995.
Malayev et al., "Mechanism of clofilium block of the human Kv1.5 delayed rectifier potassium channel", Mol Pharmaco, 147(1), 198-205, 1995.
Godreau et al., "Mechanisms of action of antiarrhythmic agent bertosamil on hKv1.5 channels and outward potassium current in human atrial myocytes", J Pharmacol Exp Ther 300(2), 612-620, 2002.
Matsuda et al., "Inhibition by a novel anti-arrhythmic agent, NIP-142, of cloned human cardiac K+ channel Kv1.5 current", Life Sci, 68, 2017-2024, 2001.
Bachmann et al., "Characterization of a novel Kv1.5 channel blocker in *Xenopus* oocytes, CHO cells, human and rat cardiomyocytes", Naunyn Schmiedebergs Arch Pharmacol, 364(5), 472-478, 2001.
Peukert S, Brendel J, Pirard B, Bruggemann A, Below P, Kleemann H W, Hemmerle H, Schmidt W. Identification, synthesis, and activity of novel blockers of the voltage-gated potassium channel Kv1.5. J Med Chem. February 13; 46(4):486-98, 2003.
Xu & Xu, "The expression of arrhythmic related genes on *Xenopus* oocytes for evaluation of class III antiarrhythmic drugs from ocean active material", Yi Chuan Xue Bao, 27(3), 195-201, 2000.
Katada et al, 'Cytotoxic effects of NSL-1406, a new thienopyrimidine derivative, on leukocytes and osteoclasts.' Bioorg. Med. Chem. Lett., 9, 797-802, 1999.
Stewart et al, 'Discovery of inhibitors of cell adhesion molecule expression in human endothelial cells. 1. Selective inhibition of ICAM-1 and E-selectin expression', J. Med. Chem., 44, 988-1002, 2001.

Hozien et al, 'Synthesis and application of some new thienopyrimidine derivatives as antimicrobial agents', Synthetic Communications, 26(20), 3733-3755, 1996.

Ismail et al., 'Synthesis and antimicrobial activity of some tetramethylenethienopyrimidine derivatives', Farmaco, 50(9), 611-616, 1995.

Konno et al., 'Synthesis of thienopyrimidine derivatives and their antifungal activities', Yakugaku Zasshi, 109(7), 464-473, 1989.

Ram et al., 'Thienopyrimidines as potential chemotherapeutic agents II', J. Het. Chem., 18(7), 1277-1280, 1981.

Ram et al., 'Thienopyrimidines as potential chemotherapeutic agents', Archiv der Pharmazie, 312(1), 19-25, 1979.

Shehata et al., 'Synthesis, antitumour and anti-HIV-1 testing of certain thienopyrimidine, thienoimidazopyrimidine and thienothiazine derivatives' Med. Chem. Res., 6(3), 148-163, 1996.

Moneer et al, 'Reaction of 30amino and 4-hydrazino-5,6-tetramethylenethienopyrimidine derivatives with azlactones', Egyptian Journal of Pharm. Sci., 34 (4-6), 599-609, 1994.

Jordis et al., '7,9-Dideaza-9-thiaadenines (4-aminothieno[2,3-d]pyrimidines) as potential anticytokinins' Vestnik Slovenskega Kemijskega Drustva, 33(3), 217-38, 1986.

Noravyan et al., 'Synthesis and anticonvulsive activity of 4-alkyl (or aryl)amino-6,6-dimethyl-5,6-dihydro-8H-pyrano (or thiopyrano)[3,4-b]thieno[5,4-d]pyrimidines' Khimiko-Farmatsevticheskii Zhurnal, 11(9), 38-42, 1977.

Hosni et al., 'Thienopyrimidines II: synthesis of newer thieno[2,3-d]pyrimidines and their quaternized derivatives with molluscicidal activity' Acta Poloniae Pharmaceutica, 56(1) 49-56, 1999.

Munchof et al., 'Design and SAR of thienopyrimidine and thienopyridine inhibitors of VEGFR-2 kinase activity'. Bioorganic & Medicinal Chemistry Letters, 14(1), 21-24, 2004.

Dobrev et al., 'The G protein-gated potassium current $I_{K,Ach}$ is constitutively active in patients with chronic atrial fibrillation.' Circulation, 112(24):3697-706, 2005.

The invention claimed is:

1. A compound selected from those of formula (Ia)

(Ia)

and enantiomers, pharmaceutically acceptable esters, wherein esterification occurs at the alcohol group, or salts thereof.

2. The compound of claim 1, wherein the compound is of formula (Ib)

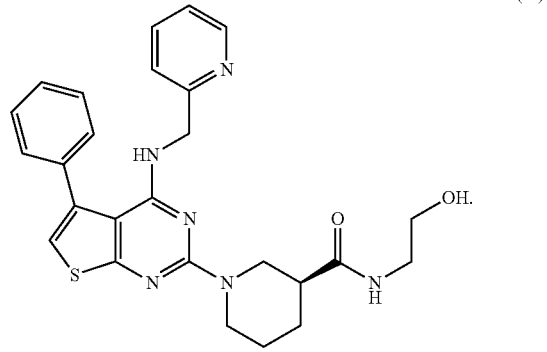

(Ib)

3. The compound of claim 1, wherein the compound is of formula (Ic)

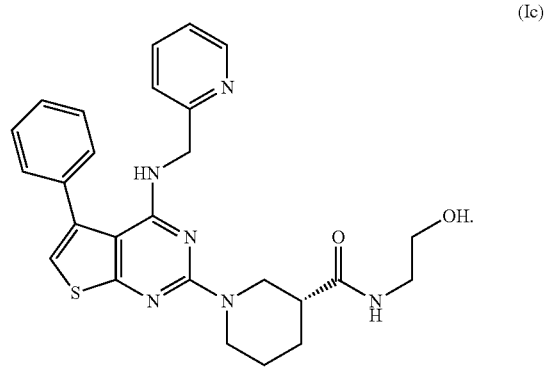 [SMILES: O=C(NCCO)[C@@H]1CCCN(c2nc(NCc3ccccn3)c3c(-c4ccccc4)csc3n2)C1]

(Ic)

4. A composition comprising a mixture of the compounds of formulae (Ib) and (Ic)

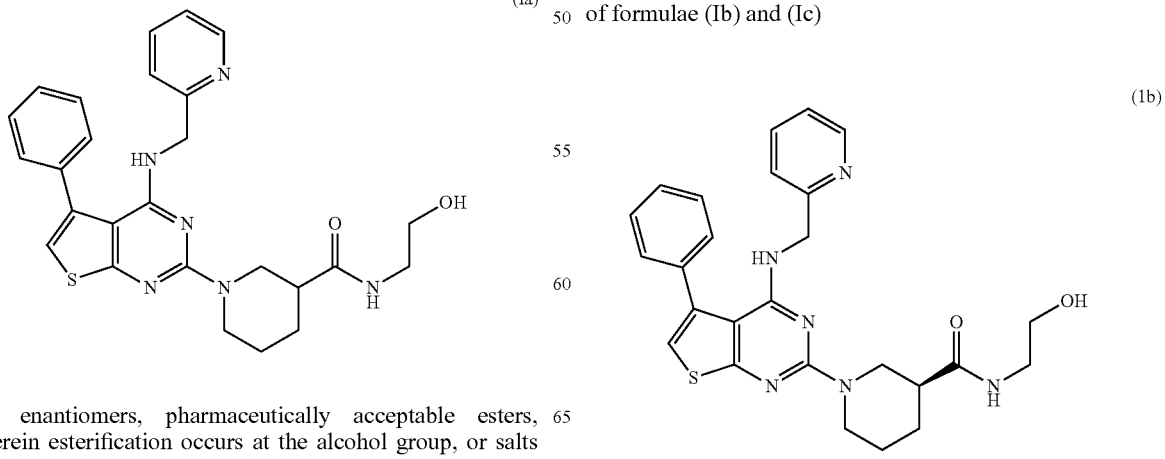

(Ib)

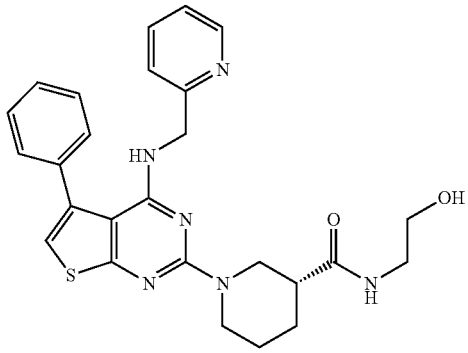

and enantiomers, pharmaceutically acceptable esters, wherein esterification occurs at the alcohol group, or salts thereof.

5. The composition of claim 4, wherein the composition comprises a racemic mixture of the compounds of formulae (Ib) and (Ic).

6. The composition of claim 4, wherein the composition comprises an enantiomeric excess of the compound of formula (Ib).

7. The composition of claim 4, wherein the composition comprises an enantiomeric excess of the compound of formula (Ic).

8. The pharmaceutical composition comprising at least one compound of claim 1 and, optionally, one or more pharmaceutically acceptable excipients.

9. A method of treating a condition requiring potassium channel inhibition, comprising administering to a subject in need thereof an effective amount of at least one compound of claim 1, wherein the condition requiring potassium channel inhibition is arrhythmia.

10. The compound of claim 1, wherein the hydrogen atom of the alcohol group is replaced with —C(O)C$_{1-6}$alkyl to form a pharmaceutically acceptable ester.

* * * * *